United States Patent [19]
Harth, III et al.

[11] Patent Number: 5,661,241
[45] Date of Patent: Aug. 26, 1997

[54] ULTRASONIC TECHNIQUE FOR MEASURING THE THICKNESS OF CLADDING ON THE INSIDE SURFACE OF VESSELS FROM THE OUTSIDE DIAMETER SURFACE

[75] Inventors: George Henry Harth, III, Wadsworth, Ohio; Donald Meade Stevens, Lovingston; Jimmy Wade Hancock, Lynchburg, both of Va.

[73] Assignee: The Babcock & Wilcox Company, New Orleans, La.

[21] Appl. No.: 526,522

[22] Filed: Sep. 11, 1995

[51] Int. Cl.⁶ .................................................... G01N 29/10
[52] U.S. Cl. ........................... 73/622; 73/629; 364/507; 364/563
[58] Field of Search .................. 73/588, 597, 598, 73/602, 609, 615, 620, 622, 623, 627, 629, 631, 633; 364/507, 563

[56] References Cited

U.S. PATENT DOCUMENTS

| | | | |
|---|---|---|---|
| 3,056,284 | 10/1962 | Marsh et al. | 73/67.8 |
| 3,942,361 | 3/1976 | Rath et al. | 73/67.7 |
| 4,189,331 | 2/1980 | Roy | 148/6.31 |
| 4,334,429 | 6/1982 | Takahashi et al. | 73/629 |
| 4,435,984 | 3/1984 | Gruber | 73/628 |
| 4,446,736 | 5/1984 | Jackson | 73/600 |
| 4,493,452 | 1/1985 | Fastner et al. | 228/158 |
| 4,507,609 | 3/1985 | Madewell | 324/230 |
| 4,603,583 | 8/1986 | Heumüller | 73/596 |
| 4,634,963 | 1/1987 | Lunden | 324/58 A |
| 4,669,310 | 6/1987 | Lester | 73/597 |
| 4,673,877 | 6/1987 | Sakamoto et al. | 324/225 |
| 4,679,430 | 7/1987 | Scott-Kestin et al. | 73/290 V |
| 4,719,808 | 1/1988 | Baumann et al. | 73/622 |
| 4,918,989 | 4/1990 | Desruelles et al. | 73/627 |
| 4,936,649 | 6/1990 | Lymer et al. | 350/96.29 |
| 4,978,223 | 12/1990 | Kutchenriter et al. | 356/284 |
| 5,108,692 | 4/1992 | Schoenig et al. | 376/159 |
| 5,132,278 | 7/1992 | Stevens et al. | 505/1 |
| 5,156,636 | 10/1992 | Kuljis | 73/597 |
| 5,225,148 | 7/1993 | Desruelles | 376/245 |
| 5,294,861 | 3/1994 | Nattermann | 310/334 |
| 5,329,561 | 7/1994 | Desruelles | 376/245 |
| 5,349,860 | 9/1994 | Nakano et al. | 73/597 |

FOREIGN PATENT DOCUMENTS

| | | | |
|---|---|---|---|
| 57-154009 | 9/1982 | Japan . | |
| 57-198005 | 12/1982 | Japan . | |
| 58-169016 | 10/1983 | Japan . | |
| 60-123712 | 7/1985 | Japan . | |
| 60-142210 | 7/1985 | Japan | G01B 17/02 |
| 1589731 | 5/1981 | United Kingdom | G01B 17/02 |

OTHER PUBLICATIONS

"Ultrasonic Testing of Materials" by J. Krautkrämer and H. Krautkrämer (1977) New York, pp. 23–26.

*Primary Examiner*—Hezron E. Williams
*Assistant Examiner*—Rose M. Miller
*Attorney, Agent, or Firm*—Robert J. Edwards; Eric Marich

[57] ABSTRACT

An ultrasonic inspection method for measuring the thickness of non-welded (non-metallurgically bonded) cladding on the inside surface of a vessel from an outside diameter surface of the vessel relies upon the occurrence of a phase change at an interface between the base metal and cladding layers to precisely determine its presence and location. By measuring the length of time for the ultrasonic pulse to propagate through the cladding material, suitable predetermined calibration standards for the cladding material in question can be used to convert the time of flight of the ultrasonic pulses through the cladding into a thickness of the cladding. The cladding thickness can be measured from an outside surface of the vessel whether or not it is empty and/or without stopping the process and/or draining it, and the method can even be employed at elevated temperatures through the use of known delay lines. Alternatively, if safe access to the interior portion of the vessel is available, an internal direct inspection can be performed to determine the thickness of the non-welded cladding using a modification of the technique in which a first multiple or second reflection signal from the base metal/cladding layer interface is used.

8 Claims, 8 Drawing Sheets

Commercial UT Instrument with Bandwidth to 20 MHz

ULTRASONIC TECHNIQUE FOR MEASURING THE THICKNESS OF CLADDING ON THE INSIDE SURFACE OF VESSELS FROM THE OUTSIDE DIAMETER SURFACE

FIELD AND BACKGROUND OF THE INVENTION

The present invention relates in general to ultrasonic inspection methods and, more particularly, to an ultrasonic inspection method for measuring the thickness of non-welded (non-metallurgically bonded) cladding on the inside surface of a vessel from an outside diameter surface of the vessel.

Cladding is applied to the interior walls of process vessels to protect the vessel base material, typically mild carbon steel, from the vessel contents. This cladding approach allows the vessels to be constructed without the expense of using the typically exotic cladding materials to make up the entire vessel wall through thickness. If the cladding fails or erodes/corrodes away, the vessel contents may quickly degrade the vessel base material. Accordingly, clad thickness is periodically examined typically by venting the vessel and cleaning it to allow human entry. The cladding inspection is typically performed from the interior surface, and is done visually or through some qualitative measure of clad thickness such as using electromagnetics.

U.S. Pat. No. 4,669,310 to Lester, assigned to The Babcock & Wilcox Company, is drawn to a method for ultrasonically measuring high temperature oxide scale on the inner surface of a fluid containing tube, and may be referred to as the NOTIS® inspection technique. NOTIS® is a registered service mark of The Babcock & Wilcox Company for "inspecting and testing boiler tubes used for steam generation". An ultrasonic pulse is directed into the tube and the time of flight of the ultrasonic pulse within the scale is determined. The time of flight is correlated to the thickness of the scale. First and second time of flights to and from the tube metal/scale interface and to and from the scale/fluid interface are determined. The difference between the first and second times of flight are correlated to determine the thickness of the scale. A high frequency transducer capable of frequencies of 50 MHz is employed, the transducer having a circular active element with a diameter of 0.250". A high frequency pulser/receiver is provided to produce high frequency pulses having a short duration with a wide (60 MHz) bandwidth. This allows production and receipt of an ultrasonic signal that is capable of resolving the energy reflected from both the tube/scale and scale/fluid interfaces. As indicated at col. 4, lines 57–69, Lester teaches that the ultrasonic test frequency employed depends upon the nominal value of the scale thickness to be measured. To resolve the interfaces, the scale thickness must be at least one wavelength of the ultrasound. Based upon a conservative approximation of the velocity of sound in steel, Table 2 of the '310 patent shows the various ultrasonic frequencies, in MHz, and the minimum scale thicknesses which can be resolved at these frequencies. The '310 patent states that the velocity of sound in scale is generally not known and will vary in scales of different compositions, which results in the fact that the time of flight technique does not produce an absolute or exact scale thickness. However, time of flight data can be related to actual scale thickness measurements established by physical techniques such as metallurgical examinations. Testing cited in the '310 patent indicates that frequencies on the order of 5–10 MHz could not be used to measure the thickness of oxide scale although testing did indicate that a highly damped 10 MHz transducer with a laboratory grade pulser/receiver and oscilloscope could detect but not measure the presence of scale on the inner surface of a boiler tube when the thickness of the scale was greater than 0.007". The scale being interrogated is produced through oxidation of the boiler tube material when exposed to high temperature, in contrast to a scale caused by accumulation of other materials on the inside of the tube, or an intentionally applied layer of material such as cladding.

Mitsubishi Japanese patent specification 60-142210 teaches a method for measuring the thickness of composite material made of zirconium alloy and zirconium using an ultrasonic wave and prescribed frequency in a line focus type probe. The tube 1 has an outer layer of material 1a made of zirconium alloy and an inner layer of material 1b made of zirconium. The tube 1 is dipped in a fluid medium 2 and an ultrasonic wave having a frequency from 20–100 MHz is emitted from the probe 3. Transmitted and reflected waves are displayed on a cathode ray tube 5 of an ultrasonic inspector 4. The ultrasonic wave is reflected at the interface between the outer layer 1a and the medium 2, as well as between the outer layer 1a and inner layer 1b, generating echoes. The thickness of the layers 1a and 1b are thus measured accurately and surely from the time intervals between the respective echoes. The Mitsubishi approach disclosed therein is thus an immersion technique, wherein the test pieces are immersed in a fluid medium for measuring the thickness of composite materials made of zirconium alloy and zirconium (i.e., a clad tube) using an ultrasonic wave and a prescribed frequency from 20–100 MHz. Ultrasonic waves are reflected at the interface between the outer and inner layers and the thicknesses of each of these layers are measured by the time interval between the echoes.

Takahashi et al. (U.S. Pat. No. 4,334,433) teaches a method and apparatus for measuring the thickness of clad steel which involves applying ultrasonic waves on the side of a sample opposite the cladding layer. Reflective waves are sensed and displayed on an oscilloscope and using a disclosed technique for eliminating noise and interference, the position of the interface between the cladding layer and the base metal layer are measured from a pulse produced due to the discontinuity of acoustic impedances at the interface. One disclosed embodiment is a case where the base metal is made of carbon steel having a small difference in its acoustic impedance from that of a cladding layer thereon which is made of stainless steel with accordingly only a very weak echo generated at the interface therebetween. Takahashi et al. teaches that it should be noted in the case of other cladding materials such as aluminum, copper, and alloys thereof, the differences of their acoustic impedances from that of the base metal are much greater than in this example and it is easier to measure the thicknesses in such cases. According to the invention, a weak interface echo is clearly separated just in front of the bottom surface echo with the precision of at least ten times that previously obtainable by amplifying the gain, enhancing the pulse output, and displaying the shape of the echo signal on an oscilloscope tube. Measurement of the thickness of any position of the clad steel within plus or minus 1 mm is obtained, from either the surface side or the back side. In particular, if the total thickness of the clad steel is more than 2.5 mm and that of cladding material is more than 0.4 mm, it is stated to be quite easy to measure both thicknesses. It is also stated to be possible to measure thickness of a material having a curvature of more than 1.5 times that of the contact detecting terminal diameter which has a cylindrical or arcuate shape.

Takahashi et al thus teaches a method and apparatus for measuring the thickness of clad steel which involves applying ultrasonic waves on the side of the sample opposite the cladding layer. The technique is particularly applicable to cases wherein the base metal is made of carbon steel having a small difference in its acoustic impedance from that of a cladding layer thereon made of stainless steel. In such a case, a very weak echo is generated at the interface therebetween. Takahashi et al can measure the thickness of the clad steel within plus or minus 1 mm.

Desruelles et al. (U.S. Pat. No. 4,918,989) teaches a method for checking the thickness of the plating on a metal tube where the plating to be checked is at least 0.4 mm thick and in which the acoustic impedance differs by at least 1% relative from that of the core of the tube. A properly dampened transducer is selected which has a frequency of 4–10 MHz. To determine the thickness of the plating, at least one double echo from the interface between the plating and the tube cores used, or alternatively a triple echo from the interface is used. Properly dampened transducers are selected which have a frequency of 4–10 MHz. Col. 2 of this patent indicates that its principal frequency is between 4 and 20 MHz. Desruelles et al. requires the tube to be pushed through an immersion tank.

Heumüller (U.S. Pat. No. 4,603,583) discloses a method for the ultrasonic testing of ferritic parts having a cladding. This patent is primarily drawn to flaw detection wherein the faults are located near the base metal and cladding interface, and involves disposing an ultrasound transmitter on a side of the part opposite the cladding which radiates longitudinal waves therefrom into the body at an angle between 70° and 86° relative to the perpendicular. The patent states that the longitudinal waves release a wave at the cladding plane traveling parallel to the interface which has never before been detected and is only minimally sensitive to structure-related backscatter so that a correspondingly large margin or ratio of signal to noise is obtained. The radiated angle can be adjusted to focus the ultrasound beam on the cladding to enhance sensitivity.

Desruelles (U.S. Pat. Nos. 5,329,561 and 5,225,148) discloses a device for checking the thickness and the cohesion of the interface of a duplex tube comprising a tubular core made from an alloy such as a zirconium alloy and covered with a covering or cladding layer made from an alloy the base metal of which is identical to the base metal of the alloy constituting the tubular core. The device is used to check geometrical dimensions of the duplex tube and, in particular, its total thickness, the thickness of the covering and cladding layer, and to detect flaws and cohesion at the interface between the covering or cladding layer and the tubular core. The method of the '561 patent combines ultrasonic and magnetic induction steps to measure the thickness of the covering layer. The total thickness of the tube is calculated from the measurements of the propagation times of the ultrasonic waves and of the thickness of the covering layer, and the cohesion of the tube at its interface is determined by analyzing the amplitude and the shape of the ultrasonic waves reflected by the covering or cladding layer. The Desruelles '561 patent, in the Background of the Invention section at col. 2, discloses that there are known ultrasonic wave "pulse-echo" techniques to check the thickness of a duplex tube based on a zirconium alloy. In one such technique, limitations are identified that measuring of cladding thicknesses of less than 0.4 mm are not possible because the ultrasonic waves used have a frequency which does not exceed 20 MHz. For cladding layers whose thickness lies between 80 and 100 μm, it is stated that ultrasonic waves at a very high frequency in the order of 100 MHz would be required. Further, in the case of jackets for fuel rods, the cladding layer and the tubular core of the duplex tubes have very similar acoustic properties, and the coefficient of reflection of the acoustic waves at the cladding/core interface is very small (generally less than 2%). The interface echo is then very small and becomes drowned out in the acoustic and electronic noise of the ultrasonic signal.

Jackson (U.S. Pat. No. 4,446,736) discloses an ultrasonic testing method to determine the integrity of the internal lining of a hollow body, especially a pipeline, by transmitting an ultrasonic pulse from the exterior of the body through the adjacent wall of the body and fluid medium therein and monitoring the wave, if any, reflected from the opposite wall. The technique is particularly adapted to determine the integrity of concrete linings within a pipe. An absence of a reflected wave indicates that the lining is intact or partially intact, while a reflected wave frequently indicates loss of the lining on an adjacent wall. However, the patent acknowledges that sometimes a reflection from the opposite wall may occur, even when the lining is intact, and in such cases comparison of the reflected wave with predetermined standards can provide an indication of whether or not the lining is indeed intact. This latter situation would involve comparing the magnitude of the reflected wave with a predetermined standard to assess the presence or absence of the lining of the wall at the point where the transmitted wave enters the wall.

U.S. Pat. No. 5,349,860 to Nakano, deceased et al. discloses an apparatus for measuring the thickness of a clad material having an outer mother metal and inner clad metal. The apparatus includes a transmitter crystal and a receiver crystal of a double crystal angle-type probe which contacts the outer surface of the mother metal, for receiving a first echo from the boundary surface of the mother metal and clad metal, and for receiving a second echo from the inner, bottom surface of the clad metal. The echo signals are amplified, a detector detects the zero-crossing points of the echoes, and the thicknesses of the clad material and clad metal are based upon the calculated periods of time for the zero point crossings. The frequency range cited is preferably in the range from 2–10 MHz, and coupling methods can be used including the contact method and the water column coupling method. Stationary, spiral or longitudinal scans can be performed.

However, Nakano, deceased et al., does not consider three problems that will be encountered in the actual application of the technique described in that patent. First, the approach disclosed depends on the setting of the "C-gate" in the region of time where the reflection, C', from the clad will be present. A user of this approach thus must have prior knowledge of the general expected time of arrival of the C' signal (which implies that the user must know the approximate clad thickness before the thickness measurement can be made) in order to define the setting of the C-gate.

Second, a user of the Nakano, deceased et al., approach assumes that the only signal present in the "C-gate" is the reflected signal from the clad interface. As illustrated in FIG. 5 of U.S. Pat. No. 5,349,860, this is an idealized depiction of the assumed reflected signals. In practical applications, there will be many reflected signals within the "C-gate" time span due to the presence of reflections from possible grain boundaries in the material and from electronic noise interference.

Third, the idealized approach of the '860 patent does not address practical applications, especially with higher frequency ultrasonic sensors or ultrasonic sensors with delay lines. Such ultrasonic sensors, especially those operating at high (15–100 MHz) frequencies, typically have artifact signals which are present even when the ultrasonic sensor is not applied to a test piece, due to small imperfections which occur during manufacture of the ultrasonic sensors. For applications requiring delay lines to provide temperature isolation, there are additional reflected signals present which arise from the sensor/delay line interface that can occur in the general time frame or area as the expected clad reflected signal. The '860 patent does not provide any method for discriminating among these various signals.

The above-identified patents typically deal with metallurgically-bonded materials. If the cladding is metallurgically connected, the laws of physics define the ratio of incident to reflected wave strength (i.e., reflectivity). FIG. 1 represents a bar chart of the values of the calculated ratios of incident to reflected wave strength (i.e., reflectivity) for different cladding materials on a mild steel base material. As will be noted from FIG. 1, for many cases the reflectivity is very small. For those approaches relying on differences of impedances, there are some base metal/cladding combinations that would be difficult if not impossible to ultrasonically inspect.

Some of the aforementioned patents cited above involve immersion-type ultrasonic techniques. Such techniques are not readily applicable for ultrasonic cladding thickness measurements on large (20–30 feet diameter, 100–150 feet tall) structures, particularly those that remain in operation. Further, traditional industry practices do not use contact methods at very high frequencies.

Ultrasonic methods for detecting the thickness of non-welded cladding on the inside surface of process vessels from the outside has been attempted by personnel in the chemical industry, but the clad/base material interface apparently could not be uniquely identified because of limitations in the approach. Referring to FIG. 2, in this approach a commercial ultrasonic test instrument 10 having a bandwidth of 20 MHz and a 20 MHz transducer 12 was used to inspect a workpiece 14 having a base metal layer 16 and an inner, non-welded cladding layer 18. On the oscilloscope display (FIG. 3) with this system, large amplitude signals are seen representative of the initial ultrasonic pulse "main bang" 20 and of the reflection 22 from the cladding/air interface at the inside wall surface of the process vessel. However, the amplitude of the signal representative of the reflection at the base metal/cladding interface (which would occur before (i.e., earlier in time and thus to the left of the displayed cladding/air interface signal) could not be distinguished and seen above the noise floor. It is believed that the rectified signals obtained with such a system do not allow the small amplitude signal representative of the base metal/cladding interface to be picked up visually.

It is thus apparent that a need still exists for an accurate, reliable ultrasonic inspection method for measuring the thickness of non-welded cladding on the inside surface of a process vessel from an outside diameter surface of the vessel.

SUMMARY OF THE INVENTION

The present invention is particularly drawn to an ultrasonic method of measuring the thickness of internal, non-welded cladding of process vessels from the outside wall of the vessel, without emptying the vessel or stopping the process stream utilizing the vessel. The measurement can be made while the vessel is operating at normal process temperatures. The method involves an ultrasonic transducer, a low noise, wide bandwidth pulser/receiver, and a high frequency oscilloscope capable of producing a non-rectified output. Preferably, the ultrasonic transducer is provided with an active area of 0.125" or greater and is operated at a frequency of 15 MHz to 100 MHz. The ultrasonic transducer is placed in direct contact with ambient temperature vessels. When elevated temperatures are encountered, delay lines capable of transmitting the ultrasound from the transducer to the vessel are employed to thermally isolate the ultrasonic transducer. The low noise, wide bandwidth pulser/receiver produces a high frequency pulse of short duration and bandwidth of up to 100 MHz. The pulser/receiver is a low noise design so that external electronic noise sources do not add to the generated or received signals at the transducer. The pulser/receiver pulses, or excites the transducer with a broadband energy pulse, which converts this electrical excitation to an ultrasonic pulse. The ultrasonic wave propagates from the outside vessel surface to the base metal/clad interface. At this interface, a first portion of the ultrasonic pulse is reflected back towards the transducer at the outside surface of the vessel. A second part of the ultrasonic pulse propagates to the inside surface of the cladding layer, which defines a second interface, where a second portion of the ultrasonic pulse is reflected back to the transducer at the outside surface. The ultrasonic transducer detects the reflected ultrasonic pulses from both interfaces and it, in combination with the pulser/receiver, converts these pulses into electrical signals.

If suitable access is available, the same approach may be used at the inside surface of the vessel, allowing the ultrasonic wave to propagate towards the outside surface of the vessel and observing the reflection/transmission of this wave from the different interfaces as it propagates back to the transducer at the inside surface. However, in such inspections, where the transducer is placed in contact (via couplant) with the cladding layer, a variation in the technique is required. This is because when thin cladding layers are being inspected, the first interface signal is usually lost in the "main bang" ultrasonic pulse provided by the transducer. Therefore, the cladding layer thickness measurement is made from the clad interface signal that appears after the second interface signal; i.e., using a third signal that is produced at the same base metal/clad interface. The high frequency oscilloscope, or any device capable of displaying high frequency waveforms in real time, can be used to display the transmitted and received waveforms. According to the invention, a human operator views the displayed waveforms representative of the two different reflected ultrasonic pulses, and can visually identify a unique signature in that waveform which is representative of the reflected ultrasonic pulse which originated at the base metal/cladding layer interface. That signal is used to determine the correct time of flight for the ultrasonic pulse to propagate through the cladding layer. By measuring the length of time for the ultrasonic wave to propagate through the cladding layer, together with suitable predetermined calibration standards, the time of flight measurement can be converted by the operator into a thickness of the cladding layer.

The primary advantage of the method of the present invention is that the clad thickness can be measured from outside of the vessel. This does not require stopping the process and/or draining the vessel contents and cleaning same to allow human entry. The measurement can be performed while the vessel is being used in processes, and even at elevated temperatures.

The present invention accomplishes the desired results due to a combination of several factors. First, the present invention employs ultrasonic signals up to the 100 MHz range, and it is believed that some of the signal strength from the interface between the base metal and the non-metallurgically bonded cladding may be occurring at this higher frequencies. The present invention is particularly directed to such non-metallurgically bonded clad situations, but still assumes that the cladding itself is in intimate contact with the base metal. In such cases, it has been determined that the ultrasonic signal itself undergoes a phase change at the interface.

The present invention relies upon the human operator visually identifying this unique, negative going signature of the non-rectified reflected ultrasonic pulse to indicate the presence and precise location of the base metal/cladding layer interface. While the signal obtained from the reflection at the base metal/cladding interface is very small, it is detectable particularly when it is recognized that the "negative going" signature of the waveform signal occurring at the interface is what can be used to identify both the presence and precise location of the base metal/cladding interface. Such phase change information is not used in the known commercial approaches, which employ rectified outputs, and none of the aforementioned patents teach that the recognition of this phase change can be used as an indicator of the presence and precise location of the interface. With the inventive method, the human operator can discriminate by determining which signals are present due only to the sensor, or sensor/delay line and, by observation, when the sensor is used on the workpiece being inspected, recognize the signature of the signal of interest, which may be of lower amplitude than the above-mentioned signals.

The various features of novelty which characterize the invention are pointed out with particularity in the claims annexed to and forming a part of this disclosure. For a better understanding of the invention, its operating advantages and specific benefits attained by its uses, reference is made to the accompanying drawings and descriptive matter in which preferred embodiments of the invention are illustrated and described.

DESCRIPTION OF THE PREFERRED EMBODIMENTS

Figure 1:
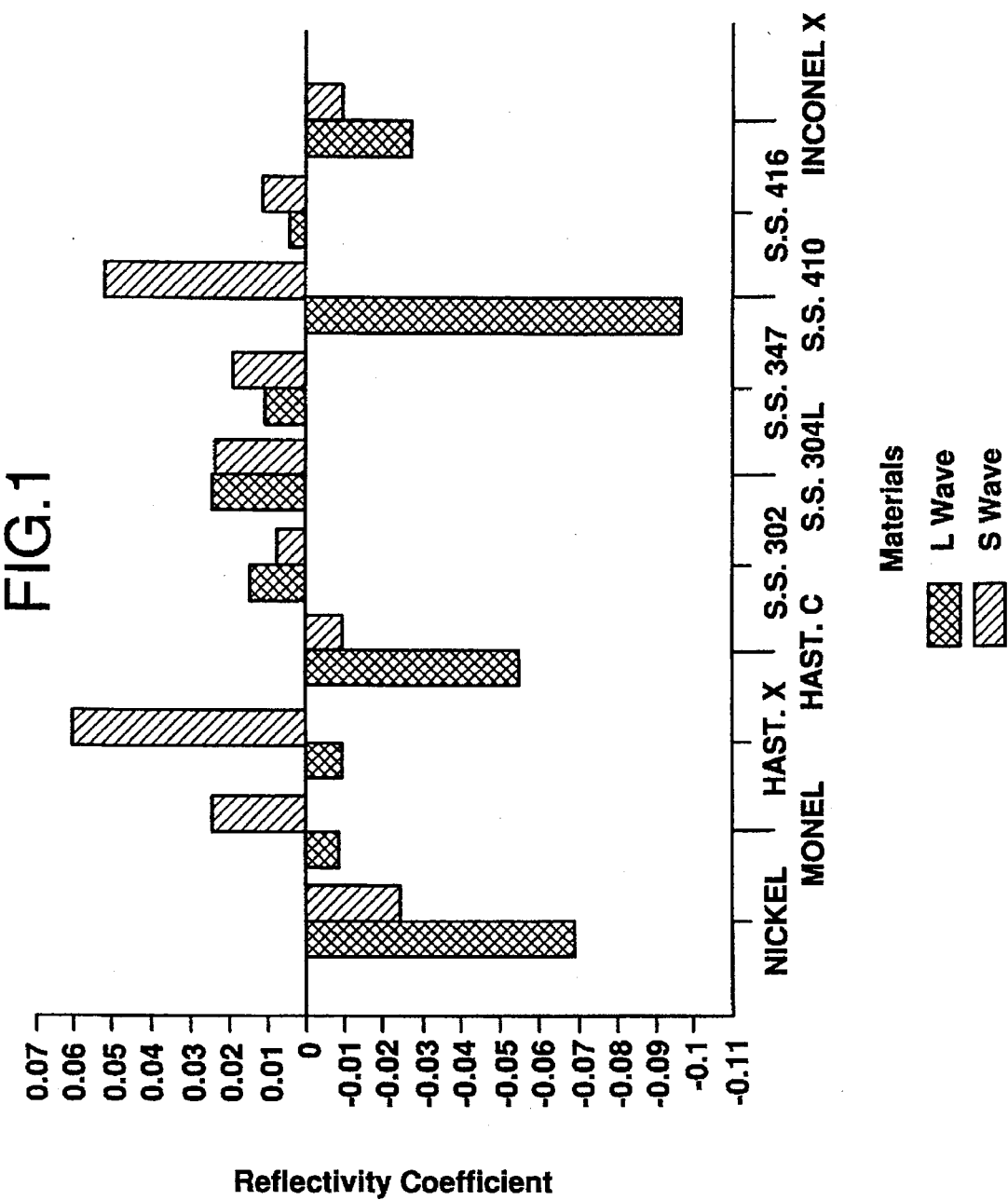
FIG. 1 is a bar chart of values of the calculated ratios of incident to reflected wave strength (i.e., reflectivity) for different cladding materials on a mild steel base material.
Figure 2:
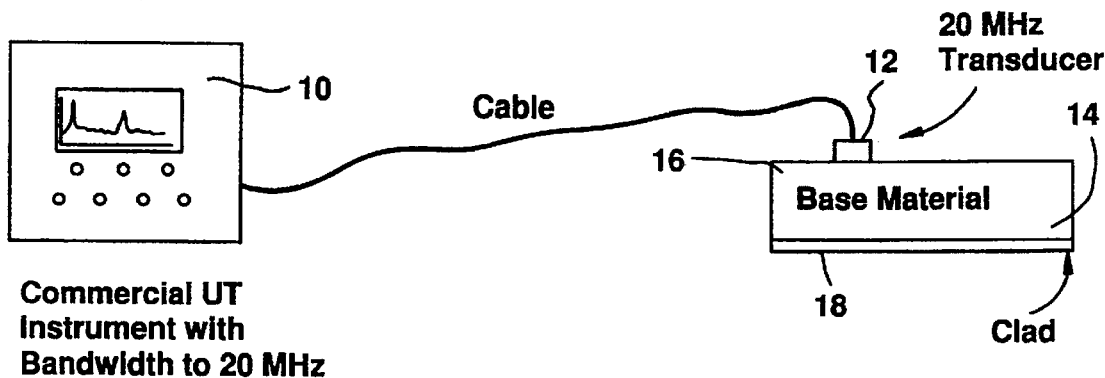
FIG. 2 is a schematic representation of a known ultrasonic system used to attempt an ultrasonic measurement of the thickness of cladding on an inside surface of a vessel from an outside diameter surface thereof.
Figure 3:
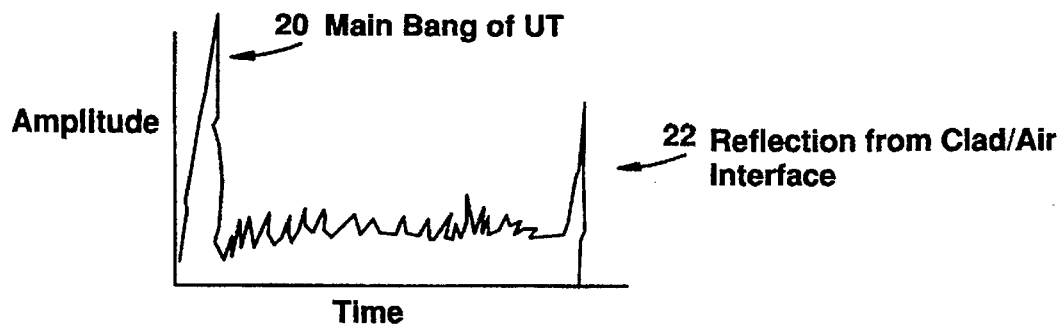
FIG. 3 is a schematic representation of an oscilloscope display of ultrasonic signals obtained using the system of FIG. 2.
Figure 4:
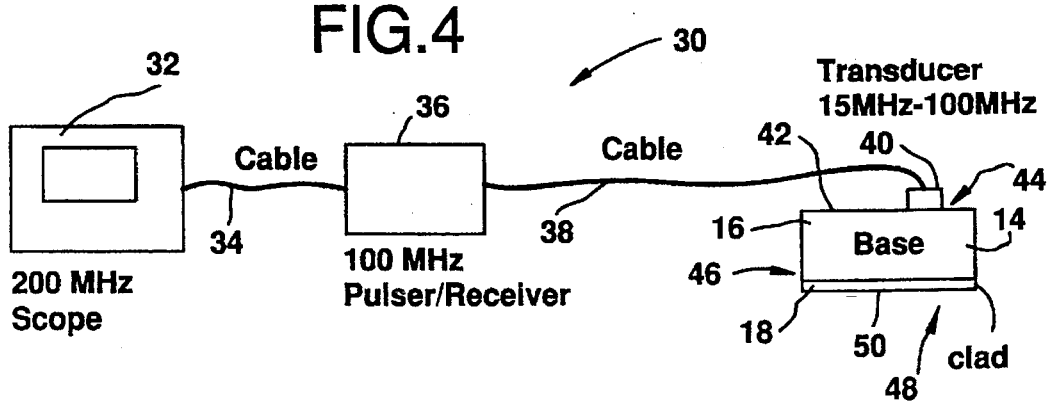
FIG. 4 is a schematic representation of an ultrasonic system used to perform an ultrasonic measurement of the thickness of non-welded cladding on an inside surface of a vessel from an outside diameter surface thereof according to the present invention.

Referring to the drawings generally, wherein like numerals designate the same or functionally similar elements throughout the several drawings, and to FIG. 4 in particular, there is shown a schematic representation of a system 30 used to practice the method of the present invention. System 30 comprises a high frequency oscilloscope 32 having a bandwidth of 200 MHz, connected by suitable cabling 34 to a low noise, wide bandwidth pulser/receiver 36. The high frequency oscilloscope advantageously comprises a Tektronix Model No. 2236 oscilloscope. The low noise, wide bandwidth pulser/receiver 36 advantageously has a bandwidth of 100 MHz and is a Panametrics Model No. 5600. Suitable known cabling 38 interconnects the pulser/receiver 36 to an ultrasonic transducer 40 preferably having an active area of 0.125" or greater and operating at a frequency of 15 MHz to 100 MHz. The ultrasonic transducer 40 is preferably a Panametrics Model No. V-214BA.

Figure 5:
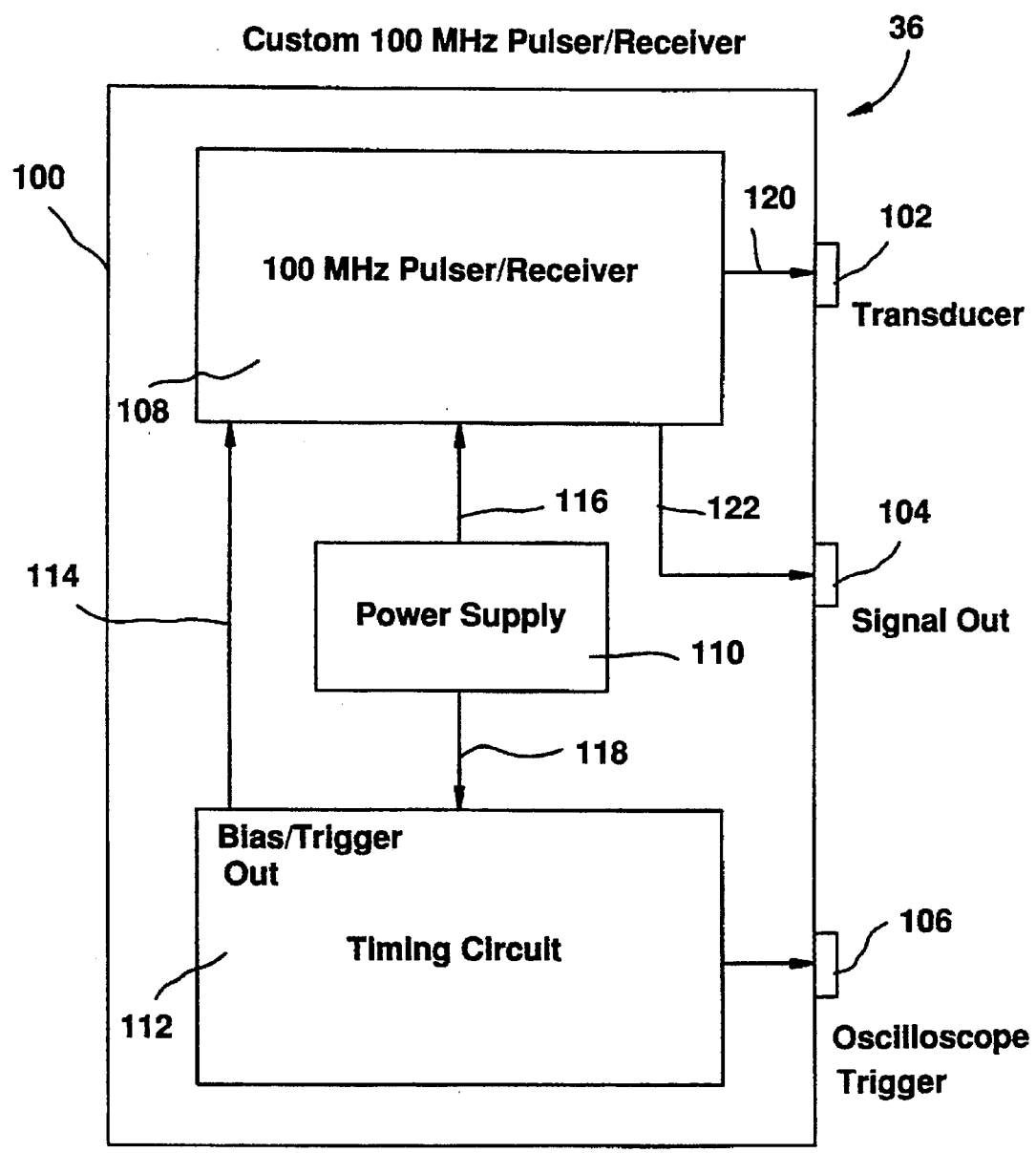
FIG. 5 is a schematic representation of the main features of a custom broadband pulser/receiver successfully used in the practice of the present invention.

A custom broadband pulser/receiver was manufactured to replace the available vendor units, such as Panametrics Model 5600. While the custom unit retains the low noise, 100 MHz bandwidth capabilities of traits like the 5600, it is packaged in a waterproof enclosure which is approximately 1/10 the size and weight of the 5600. This reduction in size is possible due to the elimination of many features found on the vendor units (stepless gates, attenuation controls, pulser voltage controls, damping, etc.). This allows the pulser/receiver to be attached to the oscilloscope and moved as one unit, and eliminates the potential for damage by inclement weather. A schematic representation of the main features of this preferred custom unit is shown in FIG. 5. Pulser/Receiver 36 includes a rugged, durable, waterproof housing 100. External connections are provided for the transducer, signal out, and oscilloscope trigger at 102, 104 and 106, respectively. Inside housing 100 are the main 100 MHz pulser/receiver board 108, power supply 110, and internal timing circuit board 112. Line 114 provides the bias/trigger output signal from timing circuit 112 to the 100 MHz pulser/receiver 108. Lines 116, 118 provide power from a power supply 110 to boards 108, 112 respectively. Lines 120, 122 are provided from 100 MHz pulser/receiver 108 to the appropriate external connections to the transducer, at 102, and to the signal out, at 104. The external power source (not shown) is typical line 120v. A.C., 60 cycles.

As shown in FIG. 4 the ultrasonic transducer 40 is applied to an outside surface 42 of the process vessel or workpiece 14, using a suitable couplant 44. A preferred couplant is SLC-70, high viscosity ultrasonic couplant, manufactured by Krautkramer Branson, which is good up to 80°–90° F. The characteristics of pulser/receiver 36 are selected so that it is a low noise source and does not produce external electronic noise sources which could be added to the generated and received ultrasonic signals from transducer 40. In operation, the pulser/receiver 36 pulses or excites the transducer 40, which converts this electrical excitation to an ultrasonic pulse. In this embodiment, the ultrasonic pulse propagates from the outside surface 42 of the vessel or workpiece 14 into the base metal 16 towards the base metal/clad interface 46. At this first interface, a first portion of the ultrasonic pulse is reflected back to transducer 40 on the outside surface 42, while another portion of the pulse continues to propagate into and through the cladding 18 towards the inside cladding/air interface 48 at the inside vessel wall surface 50. In this case, the inside cladding layer 18 has an inner surface 50 which is also the inside surface of the vessel 14, and which defines a second interface 48. While the present description has used the term cladding/air interface for the sake of convenience, vessel 14 may be empty or in operation containing or conveying any fluid, such air or other gases, or liquids. At this interface 48, a second portion of the ultrasonic signal is reflected back towards the transducer 40 located at the outside surface 42. The ultrasonic transducer 40 then detects the ultrasonic pulses from both the base metal/clad interface and cladding/air interface and it, in combination with the pulser/receiver 36, converts these pulses into electrical signals. The high frequency oscilloscope 32, or for that matter any device capable of displaying high frequency wave forms in real time, displays the transmitted and received wave forms. By measuring the time of flight of the ultrasonic pulse through the cladding 18 together with suitable predetermined calibration standards developed for the same ultrasonic test frequencies and the same (metallurgically) type of cladding material 18, the time of flight can be converted into a thickness of the cladding 18.

In certain situations, the process vessel or workpiece 14 may be at such an elevated temperature that placing the ultrasonic transducer 40 in direct contact therewith through the use of conventional or even high temperature couplants 44 is not possible. However, these situations can be addressed by utilizing delay lines (not shown) of known construction to thermally isolate the transducer 40 and yet which are capable of transmitting the ultrasonic pulses to and from the transducer 40 along the delay lines to the process vessel or workpiece 14. For such higher temperature inspections, a different type of couplant, such as Panametrics F-2 couplant could be used for temperatures of 32° F. to 540° F. As to the delay lines themselves, a typical preferred model is a Panametrics DLHT-101 delay line, and they are selected to have a desired microsecond (μs) time delay based upon the distance the ultrasound will travel in the material. Typical values for such delay lines, which are readily interchangeable (via a screw connection) on the end of the associated transducer 40, are 8 μs and 6½ μs. During an inspection, if the operator determines that the signal of interest is falling right at the signal produced by the delay line, the operator can replace it with another delay line with a different μs value, and get "off" of the overlapping area so that accurate readings can be made. As such elevated temperatures, however, even with such couplants and delay lines, the human operator must quickly take the readings and remove the transducer 40 to prevent damage to the piezoelectric element.

Figure 6:
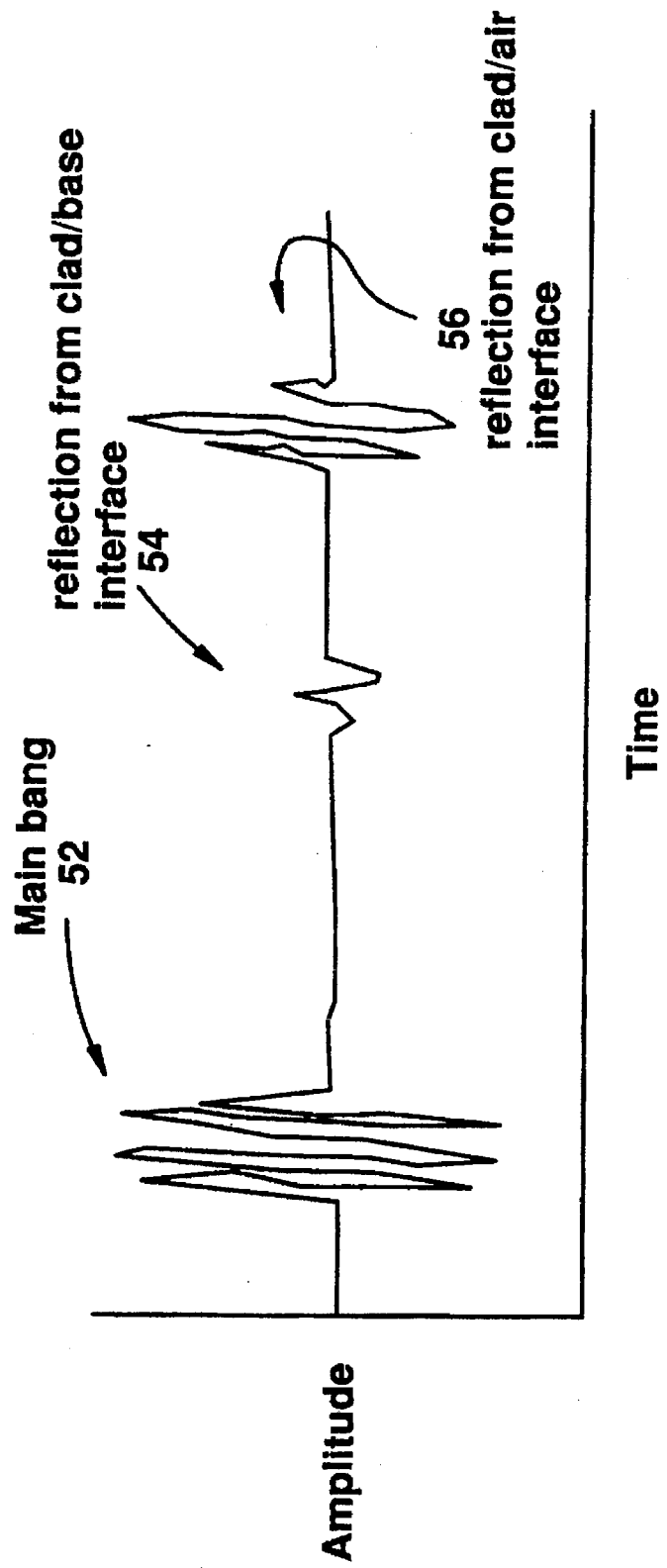
FIG. 6 is a schematic representation of an oscilloscope display of ultrasonic signals obtained using the system of FIG. 4.

FIG. 6 shows a schematic representation of an oscilloscope display of ultrasonic signals obtained using the system of FIG. 4. The "main bang" or initial ultrasonic pulse 52 is shown, along with the reflection 54 from the base metal/cladding layer interface 46, and the reflection 56 from the inside surface of the cladding layer 18. As previously indicated, the present invention is not intended for applications wherein the cladding material 18 is welded or otherwise metallurgically bonded to the base metal 16. However, the present invention assumes that the cladding layer 18 is still in intimate contact with the base material 16. In such cases, it has been discovered that the reflected ultrasonic pulse undergoes a phase change at the interface, shown in FIGS. 6–8, and this unique "signature" can be used by a human operator viewing a non-rectified display of the reflected signal to determine both the presence and precise location of the interface 46 of the base metal/cladding layer. As illustrated therein, there is a very small yet discernable "negative going" signal produced at this interface 46 where the base metal 16 and cladding material 18 are in intimate contact.

Figure 7:
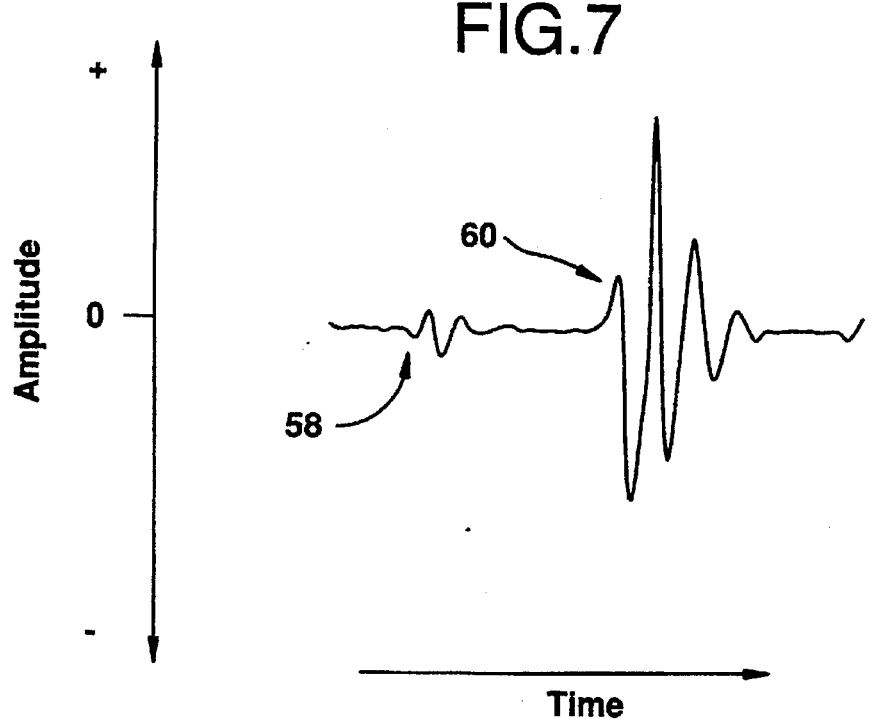
FIG. 7 is a copy of a photograph of an actual oscilloscope display obtained through use of the present invention to perform an ultrasonic measurement of the thickness of non-welded cladding on an inside surface of a vessel from an outside diameter surface thereof.
Figure 8:
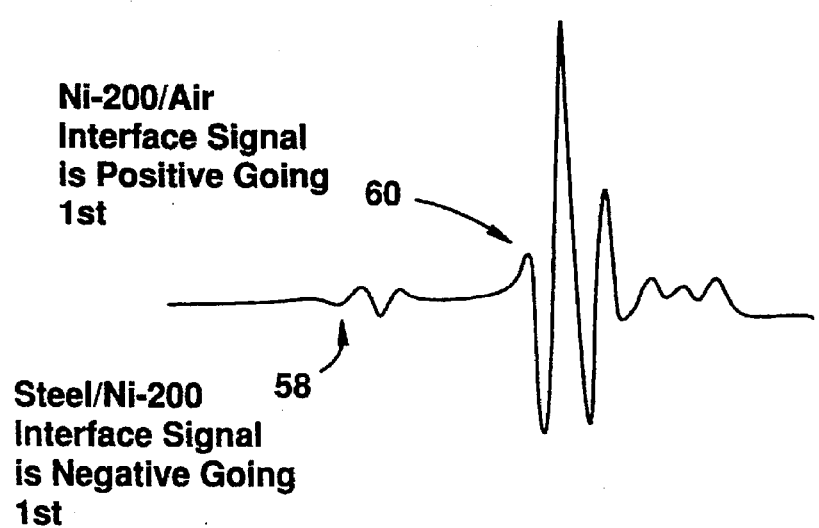
FIG. 8 is a schematic representation of the actual oscilloscope display of FIG. 7, illustrating selected features of the displayed signals.

FIGS. 7 and 8 show the oscilloscope 32 displayed signals obtained wherein steel is provided with a cladding layer of Nickel-200 material. It will be noted that at the steel/Ni-200 interface, the displayed ultrasonic signal is "negative going" first, while at the Ni-200/air interface, the displayed ultrasonic signal is "positive going" first. To the best of the inventors' knowledge, this recognition of the behavior of the received ultrasonic signals, and its use in identifying the interface between the base metal and cladding layers, was not previously known.

Figure 9:
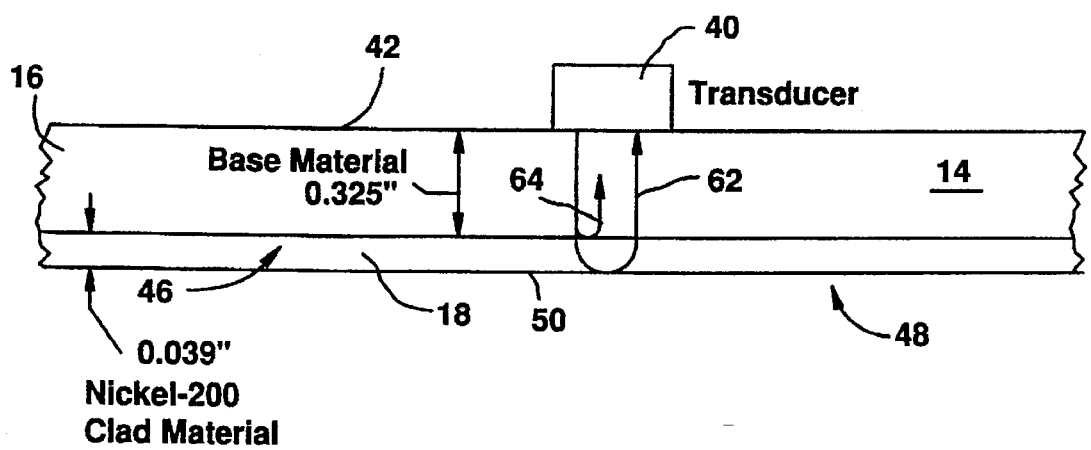
FIG. 9 is a schematic representation of an actual measurement situation wherein the present invention was used.

FIG. 9 is a schematic representation of an actual measurement situation wherein the present invention was used. The base metal 16 was 0.325" thick steel with an internal non-metallurgically bonded cladding layer 18 of Nickel 200. Reflected ultrasonic pulse 62 is reflected from the interface 48 created by and at the inside vessel wall surface 50, while reflected ultrasonic pulse 64 is reflected from the base metal/cladding layer interface 46.

FIELD TEST INSPECTION EXAMPLE

A recovery column constructed of ⅛" thick (nominal) Nickel 200 internal, non-metallurgically bonded cladding on ½" thick (nominal) carbon steel plate was inspected using the method of the present invention. Past ultrasonic thickness tests of the entire thickness of the column walls (base method+nickel cladding) ranged from 0.650" to 0.690" thick. A total of thirteen (13) external test locations were tested, at four different elevations on the column, at 4" diameter external access ports through external insulation to the column's external carbon steel metal surface provided by the recovery column owner. The test surfaces where the ultrasonic transducers 40 were placed were pre-cleaned by pneumatic needle gun. Calculated Nickel 200 cladding layer thicknesses at the various locations were relatively constant and ranged from a minimum of 0.134" thick (134 mils) to a maximum of 0.143" thick (143 mils). Subsequent physical, visual examination confirmed the correctness of these readings.

Figure 10:
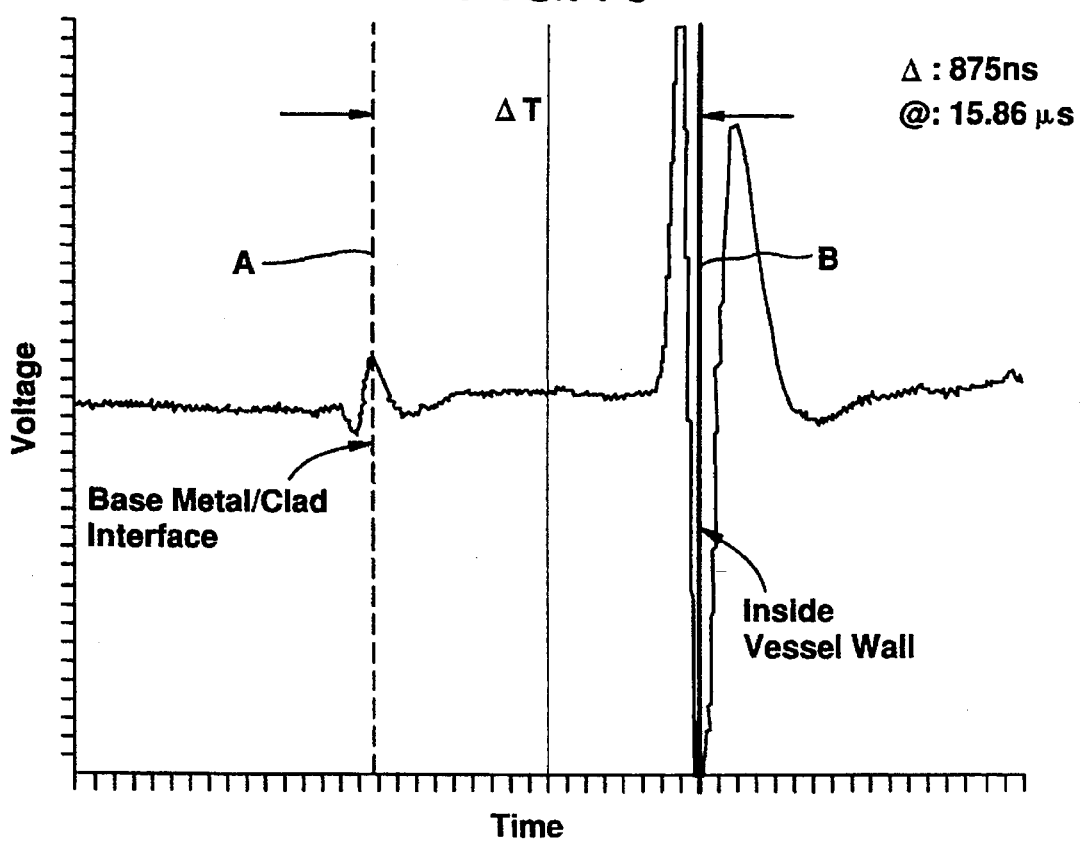
FIG. 10 is another copy of an actual oscilloscope display trace obtained through the use of the present invention, illustrating selected features of the displayed signals and particularly the time interval $\Delta T$ used to calculate the thickness of the non-welded cladding located on an inside surface of the vessel base metal wall.

FIG. 10 illustrates a copy of an actual oscilloscope display trace obtained through the use of the present invention, wherein selected features of the displayed signals and particularly the time interval ΔT used to calculated the thickness of the non-welded cladding located on an inside surface of the vessel base metal wall, as shown. As indicated earlier, the length of time for the ultrasonic wave to propagate through the cladding can be measured and used to determine the thickness thereof. Once the physical features of the workpiece being inspected are matched up to the displayed waveforms, any discernible feature such as a peak, a valley or combinations thereof can be used to gauge and measure the ΔT through the cladding layer 18. FIG. 10 illustrates a decision to use the peak of the waveform representative of the base metal/clad interface 46 and the valley, or trough of the waveform representative of the inside vessel wall surface 50. The dashed vertical line A and solid vertical line B shown in FIG. 10 are created by the oscilloscope display. The most important thing to note is that the predetermined calibration standards must be based upon the same feature convention/selection, for the same cladding material, and the same inspection frequency (and, for more accuracy, even the same transducer). Premeasured gage blocks of base metal with non-metallurgically bonded cladding (not shown) are but one example of such predetermined calibration standards.

Figure 11:
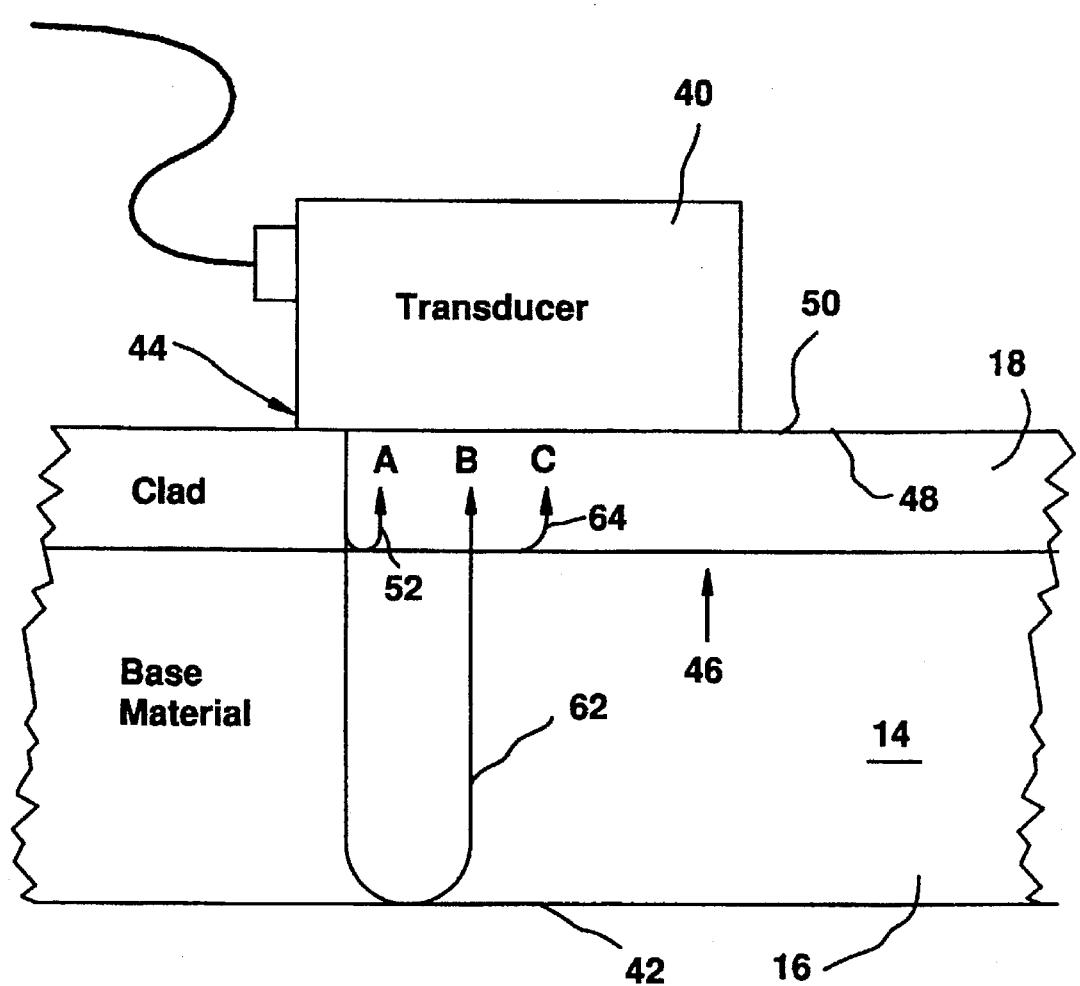
FIG. 11 is a schematic representation of a test configuration to use the present invention to measure the thickness of non-welded cladding from the surface of the cladding.
Figure 12:
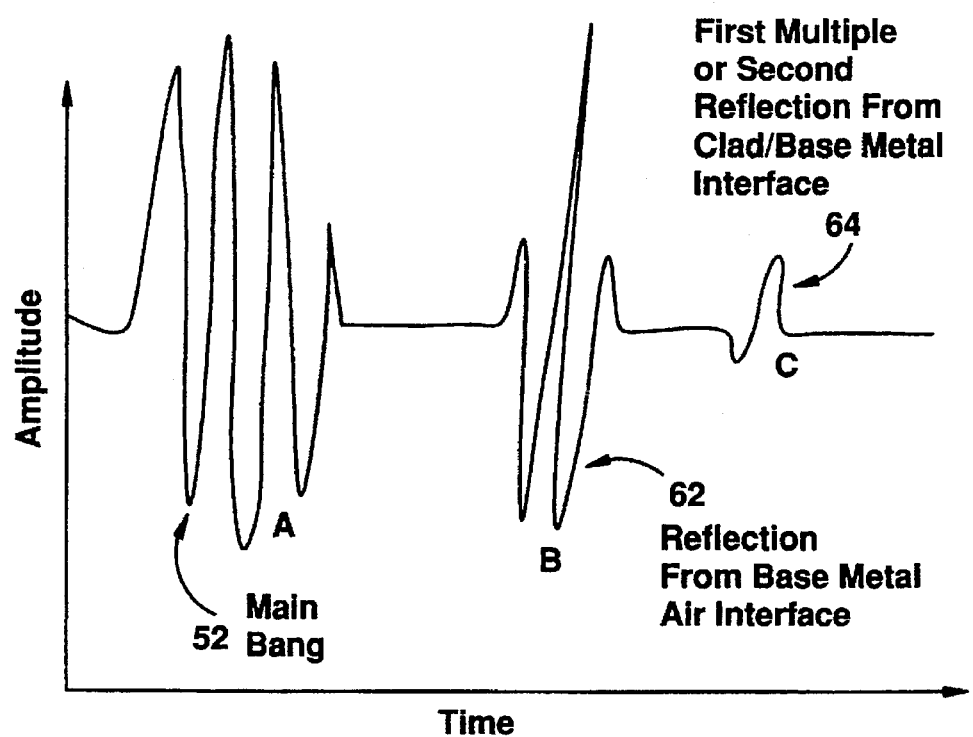
FIG. 12 is a schematic representation of an oscilloscope display of ultrasonic signals that would be obtained in the test configuration of FIG. 11.
Figure 13:
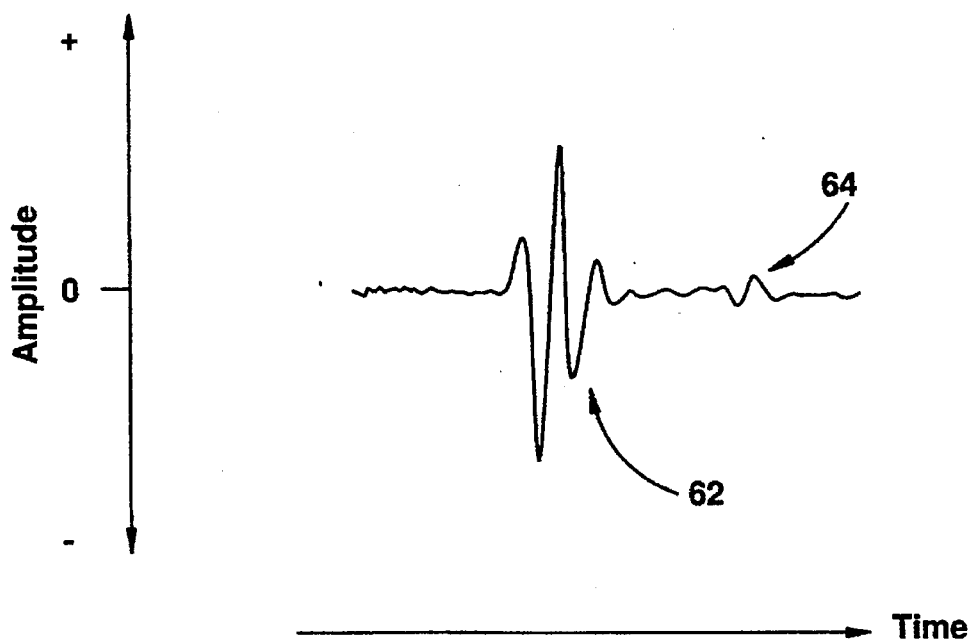
FIG. 13 is a copy of a photograph of an actual oscilloscope display obtained through use of the present invention in test configuration of FIG. 11.

Finally, FIGS. 11-13 disclose a test configuration and results obtained with such a configuration wherein the method of the present invention is used to measure the thickness of non-welded cladding from the surface non-welded cladding from the surface of the cladding itself. In such inspections, where the transducer is placed in contact (via couplant) with the cladding layer, a variation in the ultrasonic inspection technique is required. When thin cladding layers are being inspected, the first interface signal occurs so close in time to the "main bang" ultrasonic pulse produced by the transducer that the signal is usually lost and cannot be identified. Therefore, the cladding layer thickness measurement is instead made from the clad interface signal that appears after the second interface signal; i.e., using a third signal that is produced at the same base metal/clad interface.

Referring to FIG. 11, the ultrasonic transducer 40 transmits the "main bang" ultrasonic pulse into the workpiece 14 by being in contact, via couplant 44, with the clad material 18. At the base metal/cladding layer interface 46, a portion of the ultrasonic pulse is reflected back to the transducer 40 but it is lost in the "main bang" pulse 52. The balance of the ultrasonic pulse propagates into the base material 14, and is reflected at interface 42 back towards the transducer 40, and is designated 62 in FIGS. 11 and 12. However, the first multiple of the base metal/clad interface 46 occurs slightly later in time and is designated 64 in FIGS. 11 and 12. This "negative going" signal can thus be identified on the oscilloscope display and used to determine the thickness of the cladding layer 18. Alternatively, this first multiple signal from the interface can be referred to as the second reflected signal from the first interface. FIG. 13 represents a copy of a photograph of an actual oscilloscope display obtained through the use of the present invention in such a test configuration as shown in FIG. 11. However, it only illustrates the reflection from the base metal/air interface 42, and the second reflection from the base metal/cladding interface 46. Note again the "negative going" unique signature of the second reflection from the clad/base metal interface 46.

While specific embodiments of the invention have been shown and described in detail to illustrate the application of the principles of the invention, those skilled in the art will appreciate that changes may be made in the form of the invention covered by the following claims without departing from such principles. For example, while the above description uses the term outside diameter surface for simplicity, it will be readily appreciated that the invention is not limited to the inspection of cylindrical or spherical vessels or workpieces having at least one layer of base metal and another layer of non-metallurgically attached cladding, and thus the terms "vessel" and "workpiece" can be used interchangeably as the situation and application dictate without importing a limitation into the method defined by the following claims. Further, in some embodiments of the invention, certain features of the invention may sometimes be used to advantage without a corresponding use of the other features. Accordingly, all such changes and embodiments properly fall within the scope of the following claims.

We claim:

1. An ultrasonic inspection method for measuring the thickness of an internal, non-welded cladding layer of a vessel from an inside surface of a wall of the vessel, the internal cladding layer being made of a known material and having an inside surface, the vessel wall having an external layer of base metal surrounding and in intimate contact with the internal cladding layer defining a first interface therebetween, and a second interface being defined by an outside surface of the external layer of base metal, comprising the steps of:

positioning an ultrasonic transducer on the inside surface of the cladding layer within the vessel for directing an ultrasonic pulse into the wall of the vessel at an angle substantially normal to the inside surface;

energizing the ultrasonic transducer with a broadband energy pulse to transmit an ultrasonic pulse into the wall of the vessel, a first ultrasonic pulse being reflected back to the transducer by the first interface, a second ultrasonic pulse being reflected back to the transducer by the second interface and a third ultrasonic pulse being reflected back to the transducer by the first interface again as a first multiple signal occurring later in time after the second ultrasonic pulse;

receiving the second and third reflected ultrasonic pulses with a broadband receiver to produce non-rectified signals representative thereof;

displaying the non-rectified signals representative of the second and third reflected ultrasonic pulses as waveforms on a high frequency, broad bandwidth oscilloscope for viewing by an operator; and viewing the displayed waveforms and identifying a phase change of the displayed waveform representative of the second reflected ultrasonic pulse, in comparison with the displayed waveform representative of the third reflected ultrasonic pulse, as an indication of the presence and location of the first interface, measuring a time of flight of the ultrasonic pulse within the internal cladding layer, and calculating a thickness of the internal cladding layer using the measured time of flight and a predetermined calibration standard for the same type of known material as that of the internal cladding layer.

2. The ultrasonic inspection method for measuring the thickness of an internal, non-welded cladding layer of a vessel according to claim 1, comprising the step of using a predetermined calibration standard which is a tabulation of ultrasonic pulse time of flight values versus thickness through non-welded cladding made of the known material.

3. The ultrasonic inspection method for measuring the thickness of an internal, non-welded cladding layer of a vessel according to claim 1, comprising the step of positioning an ultrasonic transducer with an active area of 0.125" or greater on the inside surface of the cladding layer within the vessel.

4. The ultrasonic inspection method for measuring the thickness of an internal, non-welded cladding layer of a vessel according to claim 1, comprising the step of energizing the ultrasonic transducer with a broadband energy pulse having a center frequency of approximately 15 MHz to approximately 100 MHz.

5. An ultrasonic inspection method for measuring the thickness of a non-welded cladding layer forming a first side of a wall of a workpiece, a second side of the wall of the workpiece being formed of a layer of base metal, the cladding layer and the base metal layer being in intimate contact with each other and defining a first interface therebetween, the cladding layer being made of a known material and having an external surface defining a second interface opposite the first interface, the base metal layer having an external surface opposite the first interface, comprising the steps of:

positioning an ultrasonic transducer on the external surface of the base metal layer for directing an ultrasonic pulse into the wall at an angle substantially normal thereto;

energizing the ultrasonic transducer with a broadband energy pulse to transmit an ultrasonic pulse into the wall of the workpiece, a first ultrasonic pulse being reflected back to the transducer by the first interface and a second ultrasonic pulse being reflected back to the transducer by the second interface defined at the external surface of the cladding layer;

receiving the first and second reflected ultrasonic pulses with a broadband receiver to produce non-rectified signals representative thereof;

displaying the non-rectified signals representative of the first and second reflected ultrasonic pulses as waveforms on a high frequency, broad bandwidth oscilloscope for viewing by an operator; and viewing the displayed waveforms and identifying a phase change of the displayed waveform representative of the first reflected ultrasonic pulse, in comparison with the displayed waveform representative of the second reflected ultrasonic pulse, as an indication of the presence and location of the first interface, measuring a time of flight of the ultrasonic pulse within the cladding layer, and calculating a thickness of the cladding layer using the measured time of flight and a predetermined calibration standard for the same type of known material as that of the cladding layer.

6. The ultrasonic inspection method for measuring the thickness of a non-welded cladding layer forming a first side of a wall of a workpiece according to claim 5, comprising the step of using a predetermined calibration standard which is a tabulation of ultrasonic pulse time of flight values versus thickness through non-welded cladding made of the known material.

7. The ultrasonic inspection method for measuring the thickness of a non-welded cladding layer forming a first side of a wall of a workpiece according to claim 5, comprising the step of positioning an ultrasonic transducer with an active area of 0.125" or greater on the outside surface of the vessel.

8. The ultrasonic inspection method for measuring the thickness of a non-welded cladding layer forming a first side of a wall of a workpiece according to claim 5, comprising the step of energizing the ultrasonic transducer with a broadband energy pulse having a center frequency of approximately 15 MHz to approximately 100 MHz.

* * * * *